US010543340B2

(12) United States Patent
Fuentes

(10) Patent No.: US 10,543,340 B2
(45) Date of Patent: Jan. 28, 2020

(54) DUAL BRAID REINFORCEMENT DEFLECTABLE DEVICE (SHEATH OR CATHETER)

(71) Applicant: St. Jude Medical, Atrial Fibrillation Division, Inc., St. Paul, MN (US)

(72) Inventor: Allan Fuentes, Mound, MN (US)

(73) Assignee: ST. JUDE MEDIAL, ATRIAL FIBRILLATION DIVISION, INC., St. Paul, MN (US)

( * ) Notice: Subject to any disclaimer, the term of this patent is extended or adjusted under 35 U.S.C. 154(b) by 14 days.

(21) Appl. No.: 15/938,973

(22) Filed: Mar. 28, 2018

(65) Prior Publication Data

US 2018/0280661 A1 Oct. 4, 2018

Related U.S. Application Data

(60) Continuation of application No. 14/825,946, filed on Aug. 13, 2015, now Pat. No. 9,950,141, which is a division of application No. 13/476,841, filed on May 21, 2012, now Pat. No. 9,114,229, which is a continuation-in-part of application No. 11/618,570, filed on Dec. 29, 2006, now Pat. No. 8,182,466.

(51) Int. Cl.
*A61M 25/01* (2006.01)
*A61M 25/00* (2006.01)

(52) U.S. Cl.
CPC ...... *A61M 25/0147* (2013.01); *A61M 25/005* (2013.01); *A61M 25/0012* (2013.01); *A61M 25/0052* (2013.01); *A61M 25/0053* (2013.01); *A61M 25/0045* (2013.01); *H05K 999/99* (2013.01)

(58) Field of Classification Search
CPC .......... A61M 25/0147; A61M 25/0053; A61M 25/0052; A61M 25/005; A61M 25/0012; A61M 25/0045
See application file for complete search history.

(56) References Cited

U.S. PATENT DOCUMENTS

| 3,924,632 A | 12/1975 | Cook |
| 3,983,864 A | 10/1976 | Sielaff et al. |
| 4,709,698 A | 12/1987 | Johnston et al. |

(Continued)

FOREIGN PATENT DOCUMENTS

| JP | 08-313821 | 11/1996 |
| WO | 01/66176 | 9/2001 |

OTHER PUBLICATIONS

"Supplementary European Search Report", EP Application No. 07 865 983.6 dated Feb. 28, 2011, (6 pages).

*Primary Examiner* — Bradley J Osinski
(74) *Attorney, Agent, or Firm* — Marsh Fischmann & Breyfogle LLP; Russell T. Manning

(57) ABSTRACT

A dual braided catheter shaft includes an inner helical braid and outer helical braid than encapsulate an axially extending steering wire there between. In one embodiment, the shaft includes an inner polymer jacket, an inner braid formed on the inner jacket, a steering wire disposed along an outside surface of the inner braid, an outer braid formed over the inner braid and steering wire assembly and an outer jacket formed on the outer braid. The braiding parameters of the inner and outer braids can be varied along the length of the catheter to provide varying mechanical properties.

20 Claims, 22 Drawing Sheets

(56) References Cited

U.S. PATENT DOCUMENTS

| | | |
|---|---|---|
| 4,817,613 A | 4/1989 | Jaraczewski et al. |
| 4,981,478 A | 1/1991 | Evard et al. |
| 5,554,139 A | 9/1996 | Okajima |
| 5,569,220 A | 10/1996 | Webster |
| 5,720,301 A | 2/1998 | Van T Hooft |
| 5,755,704 A | 5/1998 | Lunn |
| 5,853,400 A | 12/1998 | Samson |
| 5,873,866 A | 2/1999 | Kondo et al. |
| 6,030,371 A | 2/2000 | Pursley |
| 6,143,013 A | 11/2000 | Samson et al. |
| 6,582,536 B2 | 6/2003 | Shimada |
| 6,582,539 B2 | 6/2003 | Iwanczyk et al. |
| 6,702,782 B2 | 3/2004 | Miller et al. |
| 6,945,970 B2 | 9/2005 | Pepin |
| 7,331,959 B2 | 2/2008 | Cao et al. |
| 7,387,629 B2 | 6/2008 | Vanney et al. |
| 7,419,489 B2 | 9/2008 | Vanney et al. |
| 7,632,256 B2 | 12/2009 | Mosler et al. |
| 7,648,462 B2 | 1/2010 | Jenkins et al. |
| 7,691,095 B2 | 4/2010 | Bednarek et al. |
| 7,914,515 B2 | 3/2011 | Heideman et al. |
| 8,376,991 B2 | 2/2013 | Kauphusman et al. |
| 2003/0191451 A1 | 10/2003 | Gilmartin |
| 2004/0097965 A1 | 5/2004 | Gardeski et al. |
| 2004/0176740 A1 | 9/2004 | Chouinard |
| 2005/0060885 A1 | 3/2005 | Johnson et al. |
| 2005/0061771 A1 | 3/2005 | Murphy |
| 2005/0065508 A1 | 3/2005 | Johnson et al. |
| 2005/0124918 A1 | 6/2005 | Griffin et al. |
| 2006/0030835 A1 | 2/2006 | Sherman et al. |
| 2007/0250150 A1* | 10/2007 | Pal .......................... A61F 2/95 604/538 |
| 2007/0299424 A1* | 12/2007 | Cumming .......... A61M 25/0012 604/527 |
| 2008/0161761 A1 | 7/2008 | Tegg |

\* cited by examiner

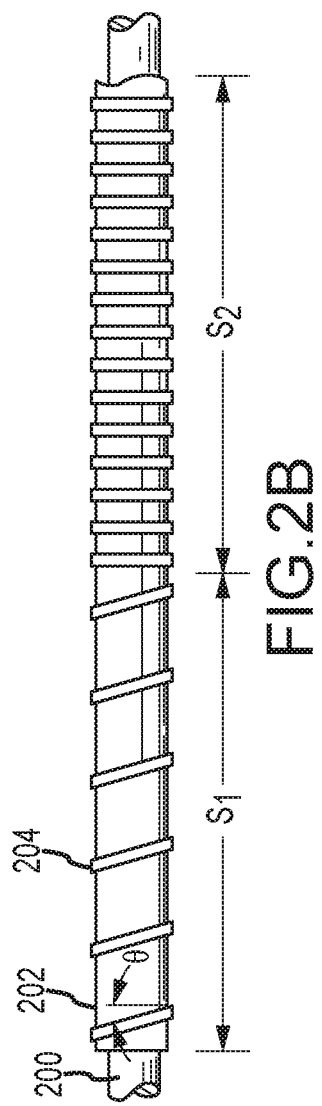

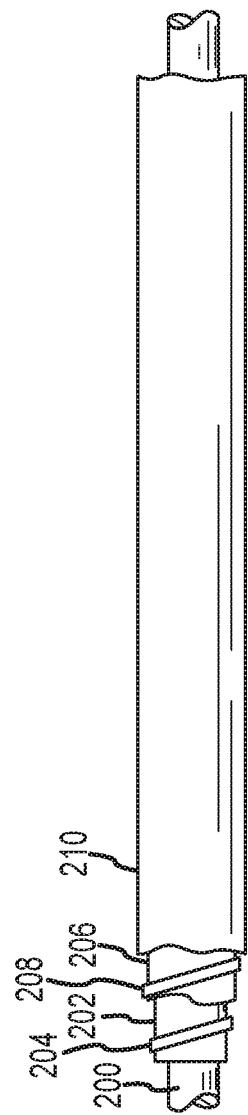

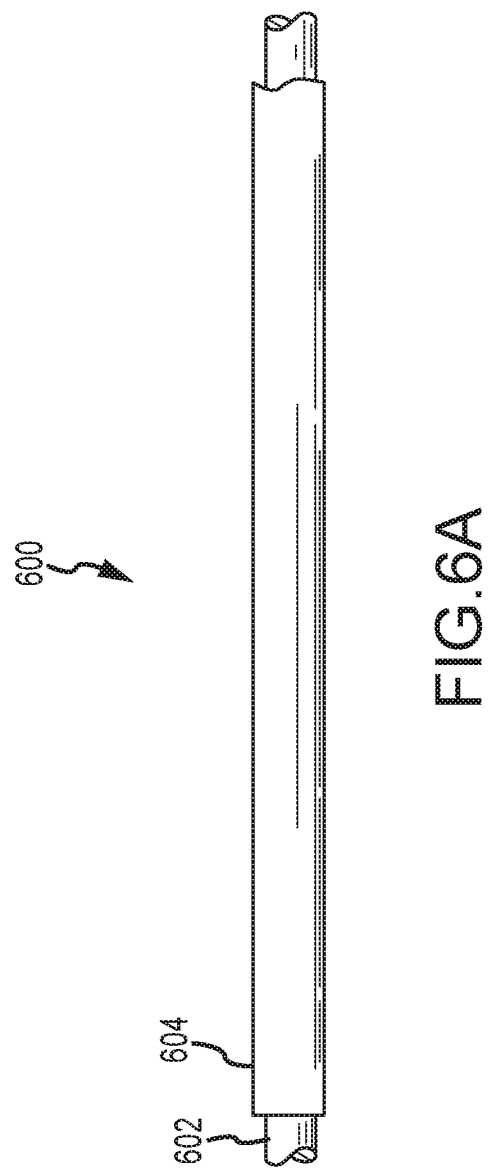

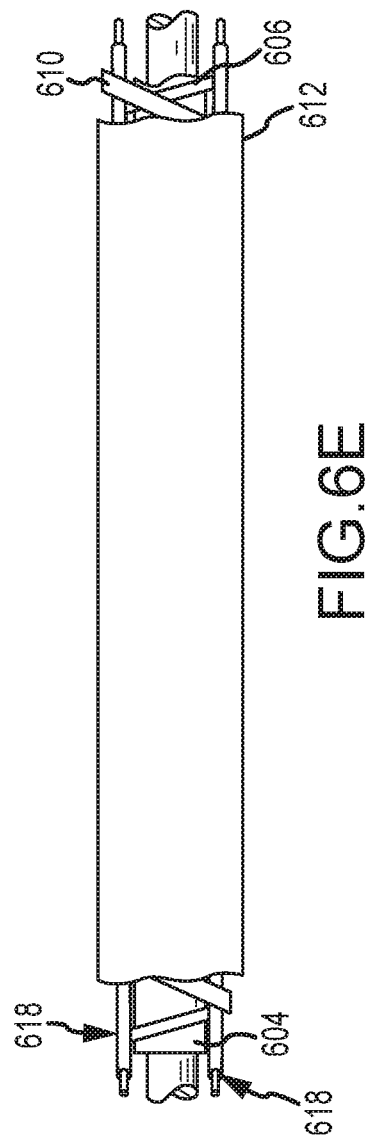

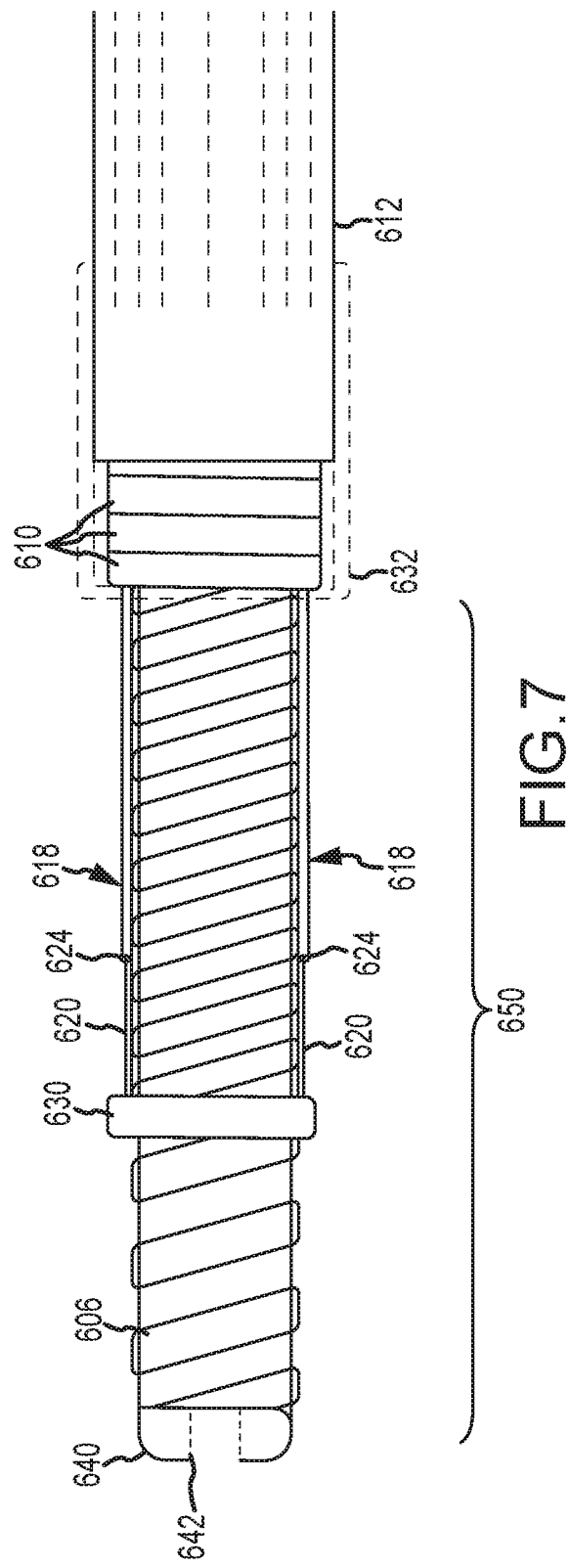

DUAL BRAID REINFORCEMENT DEFLECTABLE DEVICE (SHEATH OR CATHETER)

CROSS-REFERENCE TO RELATED APPLICATIONS

This application is a continuation application of U.S. patent application Ser. No. 14/825,946, filed Aug. 13, 2015, which is a divisional application of U.S. patent application Ser. No. 13/476,841, which issued as U.S. Pat. No. 9,114,229, which is a continuation-in-part of U.S. patent application Ser. No. 11/618,570, which issued as U.S. Pat. No. 8,182,466. The contents of the '946 application, '841 application and '570 application are hereby incorporated by reference in their entirety as though fully set forth herein.

BACKGROUND OF THE INVENTION a. Field of the Invention

The present invention relates generally to catheter shafts and, in particular, to a dual braided shaft with one or more pull or steering wires encapsulated between braid layers of the dual braided shaft.

b. Background Art

Various medical fields use different types of catheters and introducers (collectively referred to herein as "catheters") to achieve access to a physiological site for a medical procedure. For example, electrophysiology catheters are typically threaded through a blood vessel of a patient to reach a desired site for a medical procedure. In the diagnosis and treatment of atrial fibrillation, a catheter may be routed through a vessel from a patient's leg or neck to access chambers of a patient's heart. Surgical or diagnostic catheter elements, e.g., electrodes, transducers, sensors, and the like, located at the distal end of the catheter can then be used for a variety of purposes including electrical mapping and ablation. The catheter therefore may include one or more internal lumens to accommodate wires (e.g., electrode wires, pull wires for steering or other structures extending through the catheter shaft), as well as to permit irrigation as may be useful for certain procedures. Likewise, epicardial catheters are inserted into the pericardial space through a transthoracic pericardial puncture to reach the desired epicardial location.

More specifically, a catheter typically includes a handle set at a proximate end of the catheter, one or more elements associated with a distal tip at the distal end of the catheter and a shaft extending there between. The physician uses the hand set to manipulate the catheter and position elements at the desired location for the medical procedure. The shaft extends from the handle set to the distal tip through the patient's blood vessel.

The shaft is typically constructed by extruding layers of polymer onto a core rod. A metal braid may be embedded in the polymer for improved incompressibility. The core is then removed to provide a central lumen. Various wires, for example, electrode and/or pull wires are then threaded through the central lumen. Generally, each wire is threaded through the central lumen and positioned as desired within the lumen. In the latter regard, a specific relative positioning of the pull wires (e.g., diametrically opposed) may be desired for optimal performance. In addition, it may be desired to spatially separate the wires, for example, to reduce the risk of short circuits. Additional liners, cords or other structures (e.g., to define a lumen for irrigation fluids) may be inserted into the central lumen of the catheter shaft, and reflowing of the inner liner of the catheter shaft may be necessary to ensure proper adhesion. It will be appreciated that this processing is complicated and labor intensive. Moreover, there are numerous opportunities for error, which could affect catheter performance. Finally, in instances where the pull wires are held in place by a thin liner that is adhered to the internal lumen in a reflow process, the pull wires can in some instances delaminate from the inside surface of the lumen. This may be more pronounced at the ends of the pull wires where they enter and exit the catheter. In any event, the pull wires can occupy space in the internal lumen.

The catheter body or shaft is designed with a number of objectives in mind. First, the shaft is generally dimensioned with an outside diameter that allows the catheter to be threaded through the vessels necessary to perform the desired medical procedures. In addition, it is desired to provide an inside diameter sufficient to accommodate wiring, steering wiring and/or irrigation fluid channels, depending on the intended use of the catheter. Therefore, a limited radial thickness is desirable.

At the same time, the shaft should provide certain mechanical properties for optimal functioning. In particular, the shaft should resist compression during use and transmit torque. With regard to resisting compression, it is important for the physician to be able to advance the catheter through the vessel, sometimes against significant frictional resistance, without undue axial compression or snaking of the catheter shaft. Such compression can complicate positioning of the distal end of the catheter at the desired location for a medical procedure. In addition, skilled physicians often rely, to some extent, on tactile feedback to attain and verify proper positioning of the catheter, and such feedback can be impaired by excessive compressibility.

The shaft should also be capable of reliably transmitting torque. In this regard, a physician normally navigates the distal end of the catheter to a desired location in part by turning a handle set at the proximal end of the catheter. Again, substantial frictional forces sometimes resist transmission of torque across the length of the catheter. In some cases, these forces can cause the shaft to twist about a longitudinal axis of the shaft, storing energy in the process in spring-like fashion. If this energy is released suddenly, the distal end of the catheter, which may be bent by a steering mechanism, can be propelled with significant force against unintended tissue. This can have dire consequences in the context of cardiac procedures.

In order to provide the desired mechanical properties within the noted dimensional constraints, some catheters incorporate a dual braided shaft design involving an inner braided wire and an outer braided wire. The dual braided shaft is generally formed by extruding a polymer liner on a rod. The outer braid is then formed on the polymer liner, and an outer polymer jacket is then extruded onto the outer braid. Thereafter, the rod is removed to leave a hollow interior. A coil is then inserted into the hollow interior to form the inner braid, and the polymer liner is reflowed along the length of the shaft to integrate, to some extent, the inner braid into the catheter shaft structure.

BRIEF SUMMARY OF THE INVENTION

It has been recognized that there are a number of disadvantages associated with some implementations of prior art catheter construction. First, the steering wires inserted into the internal lumen of the shaft are often held in place via a secondary liner using a re-melt/reflow process that adheres the wires to the inside surface of the lumen. In some applications, these wires can delaminate from the inside surface of the internal lumen. In addition, placement of the steering wires within the internal lumen reduces the total amount of space that is available for additional wiring, irrigation, and/or passage of devices there through. This is especially acute in an introducer, where another catheter must pass through this lumen.

The present invention overcomes a number of the disadvantages associated with prior art catheter shaft construction to provide an improved catheter shaft. In particular, the present invention allows for the insertion of one or more steering wires between an inner braid and outer braid of a dual braided catheter shaft, thereby encapsulating the steering wire(s) in a sidewall of the catheter shaft. This provides a robust attachment of the steering wire to the catheter shaft and removes the steering wires from the internal lumen to a position within the sidewall of the catheter shaft. Accordingly, this may increase the available space within the lumen for other uses.

In accordance with one aspect of the present invention, a catheter apparatus is provided that includes a first wire that is wound to form an inner cylindrical braid structure and a second wire that is wound to form an outer cylindrical braid structure where the inner braid structure is disposed substantially inside of the outer braid structure. At least a first steering or pull wire is disposed between the inner cylindrical braid structure and outer cylindrical braid structure. In this regard, this first pull wire may extend along a longitudinal axis of the cylindrical braid structures. Though disposed between the first and second cylindrical braid structures, the pull wire is operative to move relative to the inner and outer cylindrical braid structures to permit, for example, actuation of a steering device of the catheter apparatus. In order to reduce the side wall thickness of the catheter apparatus as formed by the inner and outer cylindrical braid structures and the pull wire disposed there between, one or all of these wires may be formed of a flat wire having a minor cross-section dimension that is less than a major cross-sectional dimension. For example, these wires may have elliptical, rectangular, or other non-circular cross sections. In one arrangement, the pull wire(s) are disposed within or encased within a tubular sheath prior to being placed between the first and second cylindrical braid structure. In a further arrangement, the catheter apparatus further includes an inner polymer layer and an outer polymer layer. In such an arrangement, the inner and outer polymer layers may be extruded and/or re-melted to embed the cylindrical braid structures and pull wire(s) within a unitary or integral sidewall of the shaft. In any arrangement, the first and second braid structures may vary along the length of the shaft to vary mechanical properties of the shaft along its length.

In accordance with another aspect of the present invention, a catheter apparatus having a dual braided shaft is formed of a series of polymer layers and braid structures. In this regard, the apparatus includes a first cylindrical layer of polymer defining at least a first internal lumen and a first wire wound about an outside surface of the inner cylindrical layer to define a cylindrical braid structure. At least one pull wire is disposed proximate to an outside surface of the first cylindrical braid structure and extends generally along the braid structure (e.g., substantially parallel to a longitudinal axis of the first internal lumen). A second wire is wound about the outside surface of the first cylindrical braid structure and the pull wire(s) such that the pull wire(s) is encapsulated between the inner braid structure and the outer braid structure. Finally, a second outer cylindrical layer of polymer material is disposed around an outside surface and the second cylindrical braid structure. In one arrangement, the inner and outer polymer layers are preformed cylindrical polymer structures. In such an arrangement, these cylindrical polymer structures may be re-melted together to form an integral shaft structure. In another arrangement, the first and second layers of polymer material may be extruded in a continuous flow process. The catheter apparatus may further include an intermediate cylindrical polymer layer that is disposed between the first and second wires that form the inner cylindrical braid structure and outer cylindrical braid structure.

In accordance with a still further aspect of the present invention, the catheter apparatus is provided that has a proximal handle and a distal tip where a shaft extends between the proximal handle and distal tip and includes a first wire wound to form an inner cylindrical braid structure, one or more pull wires disposed on an outside surface of the inner braid structure, and a second wire wound around the inner cylindrical braid structure to form an outer cylindrical braid structure, when the pull wire(s) is encapsulated between the inner and outer cylindrical braid structures. Finally, the apparatus includes a steering or pull assembly interconnected to a distal end portion of the catheter apparatus that is operative to deflect the distal tip when actuated. An end of the pull wire interconnects to this pull assembly to provide such actuation. In one arrangement, the pull wire(s) exits from between the inner and outer braid structures prior to its attachment to the pull assembly. In a further arrangement, an end portion of the shaft may be free of the outer cylindrical braid structure.

In accordance with another aspect of the present invention, a method for use in constructing a catheter shaft is provided that involves disposing a helically wound first wire about an outside surface of a first cylindrical layer of polymer to define a first series of windings and placing one or more pull wires on an outside surface of this first series of windings. These pull wires may extend substantially parallel to a longitudinal axis of the first cylindrical layer of polymer. Once the wires are placed, a second helically wound wire defining a second series of windings may be disposed around the pull wires and the first series of windings such that the pull wire is encapsulated between the first and second series of windings. At this time, a second cylindrical layer of polymer may be disposed about an outside surface of the second series of windings. The method may further include providing a heat shrink tubing over the outside surface of the outer cylindrical layer of polymer to compress the shaft and/or re-melting the first and second cylindrical layers of polymer. Such re-melting may further include re-melting a polymer sheath disposed on the outside surface of the pull wires. Such re-melting may allow for the cylindrical layers of polymer and/or the sheaths encasing the pull wires to at least partially melt together to define a unitary or integral shaft.

In accordance with a further aspect of the present invention, a method for use in constructing a catheter shaft involves serial application of a number of layers to form a dual braided shaft. The method includes forming a first cylindrical layer of polymer material on a mandrel and braiding or winding a first wire on an outside surface of this first cylindrical layer. While the first wire is wound about first cylindrical layer of polymer, one or more pull wires may be disposed along an outside surface of this inner braid. At this time, a second wire may be wound about the outside surface of the inner braid and the pull wires to form an outer braid such that the pull wire(s) is encapsulated between the inner braid and outer braid. An additional outer layer of polymer may then be formed on the outside surface of the second braided wire. It will be appreciated that the dual braided shaft can be formed in a continuous process to define an integral system with potentially improved mechanical properties. Further, these mechanical properties of the shaft can be varied along the length of the shaft by changing the braiding parameters when braiding or winding the first and/or second wires. Thus, a dual braided shaft with variable properties along the length thereof can be formed in a continuous flow process thereby reducing construction complexity and cost.

The foregoing and other aspects, features, details, utilities, and advantages of the present invention will be apparent from reading the following description and claims, and from reviewing the accompanying drawings.

BRIEF DESCRIPTION OF THE DRAWINGS

FIGS. 2A-2F illustrate a process for constructing a dual braided shaft in accordance with the present invention.

FIGS. 6A-6G illustrate a process for constructing a dual braided shaft in accordance with the present invention.

FIG. 7 illustrates an end portion of a catheter having a steering wire encapsulated between inner and outer braids.

DETAILED DESCRIPTION OF THE INVENTION

In the following description, the invention is set forth in the context of specific implementations involving separate construction sequences for a dual braided catheter shaft and/or the incorporation of one or more pull/steering wires between inner and outer braids of the shaft, followed by assembly of those components to realize a steerable catheter. The catheter may include irrigation lumens and ports. It may also include medical elements, such as ablation elements (electrodes, transducers), sensors (electrodes, magnetic coils, thermistors) and the like. While this is an advantageous implementation of the invention, and serves to illustrate the various aspects of the invention, it should be appreciated that the invention is not limited to this catheter application, this type of catheter shaft or the illustrated construction techniques. Accordingly, the description below should be understood as exemplifying the invention and not by way of limitation.

Figure 1:
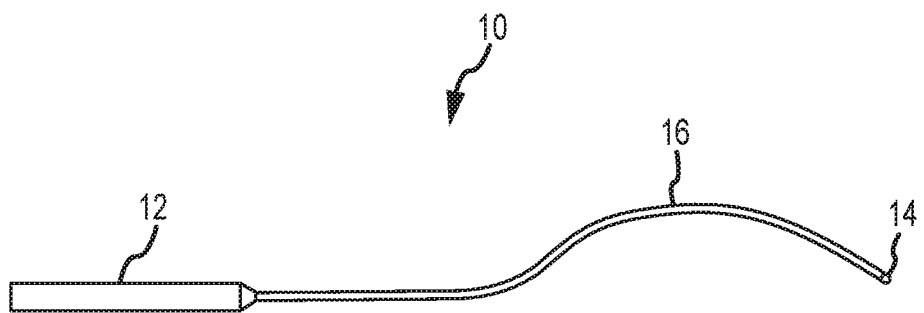
FIG. 1 shows an electrode catheter including a catheter shaft constructed in accordance with the present invention.

FIG. 1 shows an catheter 10 that may employ a catheter shaft 16 constructed in accordance with the present invention. Generally, the catheter 10 includes a handle set 12, a distal tip 14 and the catheter shaft 16 that extends between the handle set 12, at the proximal end of the catheter shaft 16, and the distal tip 14 at the distal end of the catheter shaft. The catheter 10 may include other components such as steering mechanisms, irrigation components and the like that are omitted from the drawing for the sake of simplicity.

The catheter is used to position the distal tip 14 at a desired location for a medical procedure, e.g., in the case of diagnosing or treating atrial fibrillation, the catheter tip 14 may be positioned against an internal or external wall of the patient's heart. The internal wall may be accessed, for example, by threading the shaft 16 through a blood vessel of the patient from a location in the patient's leg or neck. The external wall may be accessed by inserting the catheter into the pericardial space through a transthoracic pericardial puncture to reach the desired epicardial location. It will be appreciated that a variety of different types of electrode assemblies may be used in connection with the catheter 10 depending on the specific application involved. For example, the length of the catheter will be much shorter for a pericardial access catheter than for an electrophysiology catheter. Further, one or more ablation and/or mapping electrodes may be disposed at the distal end of the catheter shaft 16. Accordingly, the illustration of a particular distal tip 14 is not intended to imply any limitation in this regard.

In use, the physician manipulates the handle set 12 to advance, withdraw, rotate and otherwise position the distal tip 14 at a desired location. It will be appreciated that significant frictional resistance may sometimes be experienced in connection with such manipulation. In addition, experienced physicians rely to some extent on tactile feedback, transmitted back from the distal tip 14 to the handle set 12 via the shaft 16, in identifying a proper electrode position for a procedure. It is therefore desirable for the shaft 16 to be sufficiently incompressible and have sufficient torsional rigidity to allow such manipulation without substantial compression or twisting and to reliably provide the tactile feedback that is useful to physicians. The discussion below describes a suitable shaft in this regard as well as associated construction techniques.

Figure 1A:
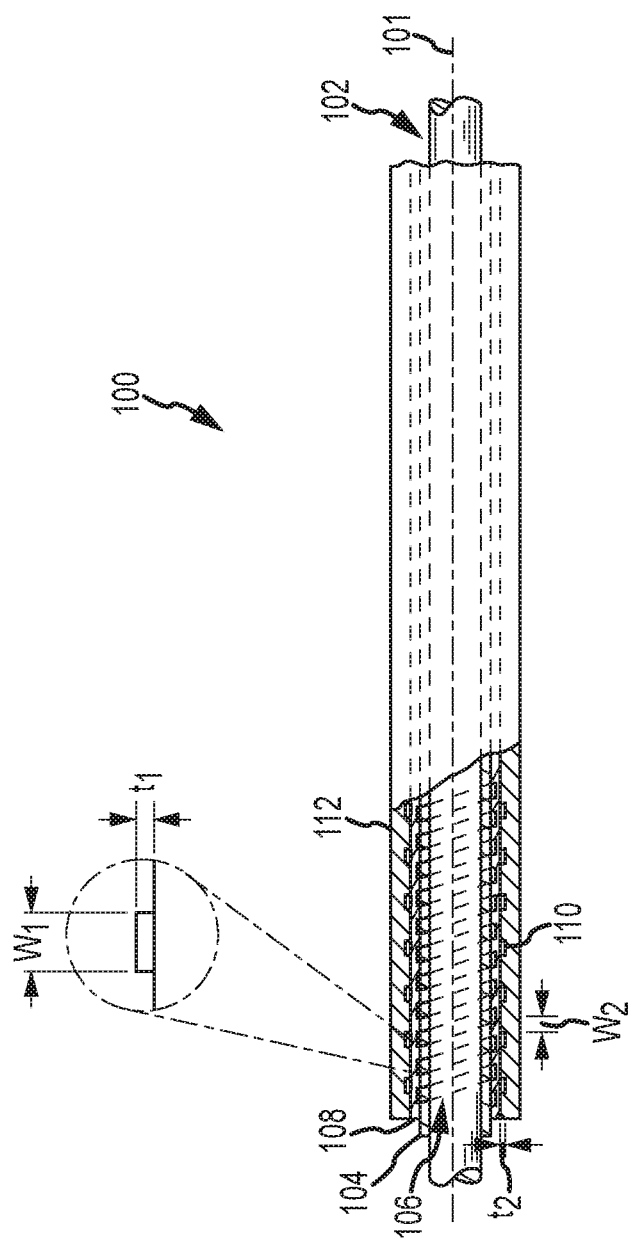
FIG. 1A is a side cross-sectional view of a dual braided catheter shaft in accordance with the present invention.

Referring to FIG. 1A, a side, partially cross-sectional view of a dual braided catheter shaft 100 in accordance with the present invention is shown. FIG. 1A also shows a core rod 102 used during construction of the shaft 100. The rod 102 is removed after construction and is not a part of the shaft 100. Rather, a central lumen remains after the rod 102 is withdrawn. This lumen may be used for a variety of purposes, including wiring for electrodes, steering wires, irrigation fluid passageways and the like. It will be appreciated that multiple lumens may be provided in the area vacated by the rod 102. Alternatively, the shaft 100 may be constructed on a hollow rod that remains as part of the shaft 100. The hollow rod defines a hollow interior for passage of irrigation fluids or wires. The hollow rod may also include a number of longitudinal channels, e.g., formed on the external surface thereof, for routing of electrode wires, steering wires and the like. The various layers of the illustrated shaft 100 can then be formed on the hollow rod.

The illustrated shaft 100 is formed from a number of layers of material sequentially formed on the core rod 102. These layers include an inner jacket 104 formed on the rod 102, an inner braid 106 formed on the inner jacket 104, an intermediate jacket 108 formed over the inner braid 106, an outer braid 110 formed on the intermediate jacket 108 and an outer jacket 112 formed over the outer braid 110. These layers 104, 106, 108, 110 and 112 thus form an integral catheter shaft system with minimal, if any, air pockets between the layers.

The inner jacket 104 is formed from a melt processable polymer extruded directly onto the rod 102. For example, the inner jacket 104 may be formed from any of various polymers having a durometer selected to impart desired mechanical properties to the shaft 100, as will be described in more detail below. Suitable polymers include those well known in the art, such as polyurethanes, polyether-block amides, polyolefins, nylons, polytetrafluoroethlyene, polyvinylidene fluoride and fluorinated ethylene propulene polymers, and other materials. A braiding machine can then be operated to wind a wire around the inner jacket 104 so as to form the inner braid 106. For example, the inner braid 106 may be constructed by winding a flat wire formed from any of various metals such as stainless steel.

The second jacket 108 is formed from a melt processable polymer (examples set forth above) and can be extruded over the inner jacket 104 and inner braid 106. In this manner, the inner braid 106 is preferably embedded in the intermediate jacket 108 with few or substantially no air pockets for potentially improved mechanical characteristics, i.e., the intermediate jacket 108 extends between successive windings of said inner braid 106 so as to contact opposite facing surfaces of the windings. The material used for the intermediate jacket 108 can be the same as or different than the inner jacket 104, and it can have the same or a different durometer.

After the intermediate jacket 108 has been formed, a braiding machine can be operated to wind a wire on the intermediate jacket 108 to form the outer braid 110. For example, a flat wire formed from metal such as stainless steel can be used in constructing the outer braid 110. The material of the wire used to form the outer braid 110 can be the same as or different than the material used to form the wire of the inner braid 106. In addition, the dimensions and winding parameters of the outer braid 110 can be the same as or different than those for the inner braid 106. Some considerations in this regard will be discussed in more detail below.

Each of the braided wires is typically embedded, to some extent, in a polymer so that the braided wire and polymer function as a system to impart desired mechanical properties. More specifically, the inner braided wire system is typically the primary source of compression resistance. The outer braided wire system, having a larger moment arm relative to the longitudinal axis of the shaft, is typically the principal source of torque transmission. Each of the inner and outer braided wire systems may be designed to satisfy its primary function in this regard.

After the outer braid 110 has been applied, the outer jacket 112 is formed on the intermediate jacket 108 and outer braid 110. For example, the outer jacket 112 may be formed from a melt processable polymer (examples set forth above) and may be extruded directly onto the intermediate jacket 108 and outer braid 110. In this manner, the outer braid 110 is substantially fully embedded in the outer jacket 112 with few or substantially no air pockets therebetween for potentially enhanced mechanical properties. The outer jacket 112 may be formed from the same material as the intermediate jacket 108 and/or inner jacket 104 or different materials may be used. In addition, the outer jacket 112 may have the same or a different durometer than the intermediate jacket 108 and/or inner jacket 104.

The properties of the various layers 104, 106, 108, 110 and 112 can be selected to impart desired properties to the completed shaft 100. In this regard, it is generally desirable that the shaft 100 be substantially incompressible. In addition, it is generally desired that the shaft 100 effectively transmit torque across the length of the shaft so that a torque applied by a physician on the handle set at the proximate end of the shaft is effectively transmitted to an electrode or other tool at the distal end of the shaft. That is, the shaft should resist twisting about the longitudinal axis 101 of the shaft 100 in the event of significant frictional resistance to such torque. On the other hand, it is generally desired that the shaft 100 (including a dual braided body section defined by the inner braid 106, intermediate jacket 108 and outer braid 110) be sufficiently flexible to allow for threading through a blood vessel of a patient and steering of the distal end of the catheter to a desired location for a medical procedure. The mechanical properties of the shaft 100 may vary along a length of the shaft in this regard, i.e., the dual braided body section may have a first value of a mechanical property at a first portion and a second value, different from the first value, at a second portion thereof.

It will be appreciated that any and all of the layers 104, 106, 108, 110 and 112 may be involved in providing the desired properties. However, in the illustrated embodiment, the inner braid system provides the primary axial rigidity for the desired incompressibility (e.g., a first mechanical property of the catheter), and the outer braid system, which has a greater moment arm in relation to the axis 101, provides the primary torsionally rigidity for transmitting torque (e.g., a second mechanical property of the catheter). As previously noted, the parameters of these braids may be altered independently along the length or longitudinal section of the catheter to vary the properties of the catheter. The inner braid system includes the inner braid 106 and the intermediate jacket 108 that is extruded onto the inner braid 106. These components cooperate to provide a desired level of axial rigidity. That is, these components may cooperate to provide a first mechanical property to the catheter. Thus, the axial rigidity of the inner braid system is principally determined by the durometer of the intermediate jacket material, the material and dimensions of the wire used to form the inner braid 106, and the braiding parameters including the pic rate (number of windings per inch) of the inner braid 106. That is, a first mechanical property of the catheter may be a function of the dimensions of the first wire and/or material properties of the polymer. With regard to the material used to form the intermediate jacket 108, the higher the durometer of this material, the greater the axial rigidity of the inner braid system, all other factors being equal. Again, it is noted that a catheter designer may balance the need for shaft flexibility with the desire for axial rigidity.

Figure 1B:
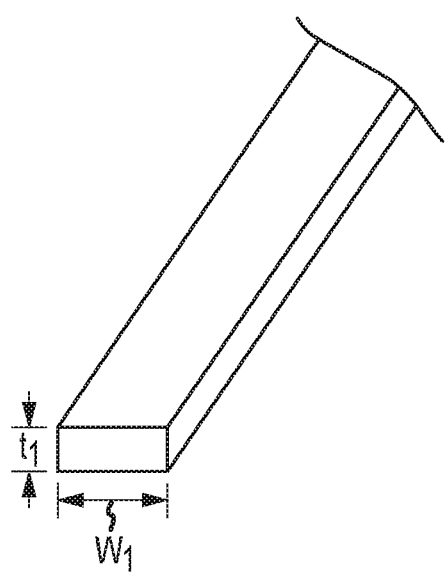
FIG. 1B is a perspective view of a wire used to form a braid of the shaft of FIG. 1A.

With regard to the material used to form the inner braid 106, generally, the harder the material the greater the axial rigidity. The axial rigidity can also be enhanced by increasing the width $w_1$ (the axial dimension) of the wire used to form the inner braid 106 and increasing the pic rate of the inner braid 106. However, it is desirable that the thickness $t_1$ (the radial dimension) of the wire used to form the inner braid 106 should be minimized to as to reduce the overall thickness of the shaft 100. Accordingly, as shown in FIGS. 1A and 1B, using a flat wire where the width $w_1$ is greater than the thickness $t_1$ allows for obtaining the desired axial rigidity without unduly increasing the thickness of the shaft 100. In the illustrated example, the thickness $t_1$ may be between about 0.00075-0.005 inches, and the width $w_1$ may be between about 0.003-0.020 inches, depending on the particular catheter application. In one embodiment, the width $w_1$ may be twice the thickness $t_1$. If additional axial rigidity is needed, but the shaft cannot be made more thickly, the width $w_1$ may be three times the thickness $t_1$.

Additionally, as will be discussed in more detail below, the pic rate may be varied along the length of the catheter, for example, to provide greater flexibility near the distal end of the catheter and greater axial rigidity towards the proximate end of the catheter. For example, depending on the application, the pic rate of the inner braid 104 may be between about 25-70 pics per inch (PPI), and this value may vary along the length of the shaft 100.

Similarly, the mechanical properties (e.g. second mechanical properties) imparted to the shaft 100 by the outer braid system are principally a function of the durometer of the outer jacket material, the dimension (e.g., thickness $t_2$ and width $w_2$, see FIG. 1A) of the outer braid wire, and the braiding parameters of the outer braid including its pic rate (which may vary along the length or longitudinal section of the shaft). Although the outer braid 110 is shown as being formed from a flat wire, a round wire or other configuration may be employed. In this regard, it is noted that a primary function of the outer wire is to impart torsional rigidity, and a greater thickness $t_2$ may be desired within the constraints of the desired overall shaft thickness. In the illustrated embodiment, the outer braid wire has a thickness $t_2$ of between about 0.00075-0.003 inches, a width $t_2$ of between about 0.003-0.020 inches, and the outer braid has a pic rate of between about 30-60 PPI. Thus, the inner braid 104 can have a first relationship of pic rate as a function of length of the catheter body and this outer braid 110 can have a second relationship, different than the first relationship, of pic rate as a function of length of this catheter body.

The resulting shaft 100 provides the desired incompressibility and torsional rigidity properties within a reduced thickness envelope, thereby allowing for a reduced shaft outside diameter and/or an increased shaft inside diameter. In this regard, the outside shaft diameter may be no more than about 5-10 French. The inside diameter may be at least about 3-8 French, and the shaft wall thickness (the outside diameter less the inside diameter) may be about 0.008 inches.

Figure 2C:
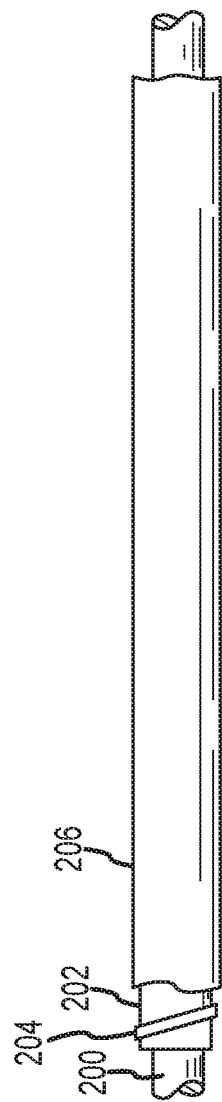

FIGS. 2A-2F graphically depict a first sequence for constructing a dual braided catheter shaft 212. As shown in FIG. 2A, the process is initiated by extruding a melt processable polymer onto the core shaft 200 to form an inner jacket 202. Thereafter, a braiding machine is operated to braid a wire onto the inner jacket 202 to form the inner braid 204. As shown in FIG. 2B, it is possible to control the operation of the braiding machine to provide a first pic rate in a first section $s_1$ of the catheter and a second pic rate in a second section $s_2$ of the catheter. In this case, a lower pic rate is used in section $s_1$ than in section $s_2$. For example, this may be done to provide greater flexibility at a distal end of the catheter and a greater axial rigidity at a proximate end. In this regard, the greater density of wire coverage in section $s_2$ provides a higher axial rigidity whereas the lesser density of wire coverage in section $s_2$ and the greater winding angle $\theta$ provides greater flexibility in section $s_1$.

Figure 2D:
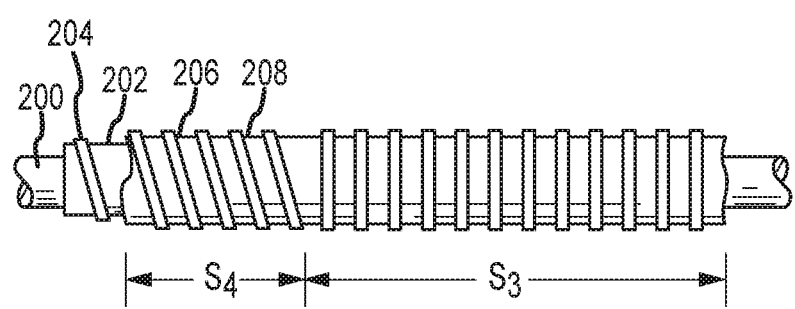

After the inner braid 204 has been formed, the intermediate jacket 206 is extruded onto the inner braid 204 and the inner jacket 202, as shown in FIG. 2C. A braiding machine can then be operated to wind a wire on the intermediate jacket 206 to form the outer braid 208, as shown in FIG. 2D.

It will be appreciated that the pic rate of the outer braid 208 can also be varied along the length of the catheter to balance the desire for torsional rigidity with desire for flexibility, as shown by the varied pic rate between $s_3$ and $s_4$. In addition, although the inner and outer braids 204 and 208 are shown as being wound in the same rotational sense in FIG. 2D, the braids 204 and 208 may be wound in opposite rotational senses, for example, to provide desired mechanical properties to the shaft 212.

Figure 2F:
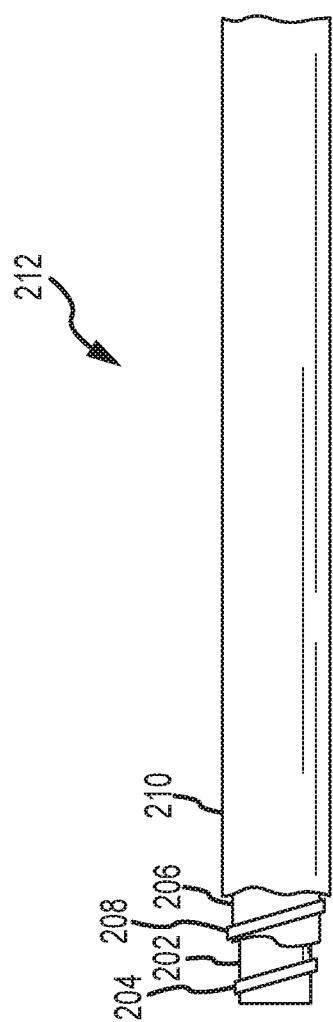

After the outer braid 208 has been formed, an outer jacket 210 is formed over the outer braid 208 and intermediate jacket 206 by extruding melt processable polymer material thereon, as shown in FIG. 2E. Finally, the core rod 200 is extracted from the assembly to form the catheter shaft 212, as shown in FIG. 2F.

Figure 3:
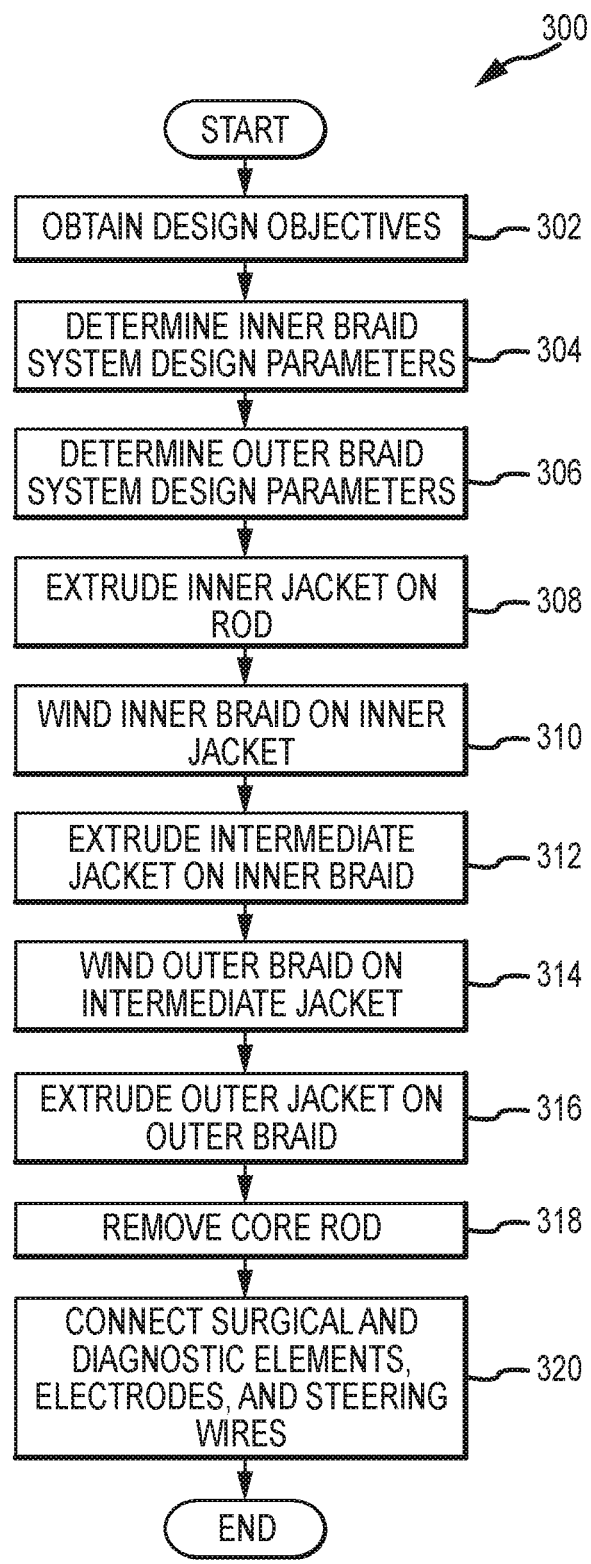
FIG. 3 is a flowchart illustrating a process for constructing a dual braided shaft in accordance with the present invention.

The overall process for designing and constructing a catheter shaft can be summarized by reference to the flowchart of FIG. 3. The illustrative process 300 is initiated by obtaining (302) design objectives for the catheter shaft. In this regard, different shaft platforms may be used for different catheter applications such as fixed curve catheters, steerable catheters, bi-directional catheters and the like. For example, the particular catheter application may dictate the need for greater flexibility or greater torsional rigidity, or may dictate a particular need for axial rigidity. In addition, the catheter application may dictate a particular limit on the outside diameter of the catheter or require an inside diameter sufficient for electrode wiring, steering wires and irrigation fluid channels. All of these objectives may be considered in relation to the design of the catheter shaft.

The designer can then determine (304) the inner braid system design parameters and determine (306) the outer braid system parameters. As noted above, the inner braid system may be used primarily to address considerations related to axial rigidity. In this regard, the durometer of the intermediate jacket material, the material used for the inner braid wire, the dimensions of the inner braid wire and the braiding parameters for the inner braid may be selected in relation to the desire for axial rigidity, on the one hand, versus catheter flexibility on the other. As illustrated above, these characteristics may vary along the length of the catheter. While it is theoretically possible to change the durometer of the intermediate jacket material along the length of catheter, as a practical matter, existing extrusion processes generally do not provide sufficient accuracy in this regard. Accordingly, in accordance with the present invention, the pic rate of the inner braid can be controlled to allow for variation of mechanical properties along the catheter shaft in a continuous flow process.

Similarly, the outer braid system design parameters can be determined (306) in relation to the durometer of the outer jacket, the material used for the wire of the outer braid, the dimensions of the wire for the outer braid and the braiding parameters used in braiding the outer braid. These parameters may be selected to balance the desire for torsional rigidity with the desire for shaft flexibility.

After the design parameters have been determined, construction of the shaft begins by extruding (308) the inner jacket on the core rod. A braiding machine is then operating to wind or cross-braid (310) the inner braid on the inner jacket. The intermediate jacket is then formed by extruding (312) material on the inner braid an inner jacket. A braiding machine can then be again operated to wind or cross-braid (314) the outer braid on the intermediate jacket. Finally, the outer jacket is extruded (316) on the outer braid and intermediate jacket, and the core rod is removed (318) to form the catheter shaft.

Surgical and diagnostic elements, such as electrodes, transducers and steering wires can then be connected (320) to form the finished catheter product. The nature of these connections and additional processes will depend on the particular catheter application. For example, steering wires may be threaded through the central lumen of the catheter shaft in the case of a steerable catheter application. In addition, wiring for a single electrode or multiple electrodes may be threaded through the central lumen, depending on the application. Additional processes may be performed to define a passageway for irrigation fluid to support irrigated medical procedures. Additional reflowing steps may be required to adhere the distal catheter tip to the distal end of the catheter shaft after the forming any necessary electrode connections. It will be appreciated that a number of other conventional finishing processes may be implemented in this regard.

In a further aspect of the present invention, it has been recognized that use of a dual braided shaft may provide additional benefits for a catheter apparatus. Specifically, it has been recognized that the inner braid and outer braid of such a dual braided shaft may be utilized to securely affix one or more pull wires or steering wires relative to the catheter shaft. As may be appreciated, in most catheter applications, such steering wires are disposed through the internal lumen of the catheter shaft once the shaft is formed and the core rod is removed. That is, such steering wires are often attached within the shaft after the shaft is formed. For instance, one or more steering wires may be inserted into the central lumen of the catheter shaft. A reflowing or re-melting of the inner liner or jacket of the catheter shaft is typically necessary to adhere the steering wires to the catheter shaft. Maintaining a desired spatial relation between the steering wires and the interior of the catheter shaft during the re-melting process is difficult and labor-intensive. Furthermore, such re-melt adherence of the steering wires within the internal lumen may, in some cases, provide a low level of adhesion such that delaminating of the steering wire from the internal surface of the catheter lumen is possible. Finally, insertion of the steering wires through the internal lumen occupies space within the lumen that may otherwise be utilized by, for example, irrigation lumens or open passageways through which additional devices may pass through the catheter.

The present invention recognizes that disposing the steering wires between the inner braid and outer braid of a dual braided catheter shaft alleviates these problems. That is, once so disposed, the steering wires are securely held in place between the inner and outer braids, eliminating concerns of delaminating. Furthermore, the steering wires are removed from the internal lumen and disposed into a sidewall of the catheter shaft. Accordingly, there may be additional space available within the central lumen for other uses.

Figure 4:
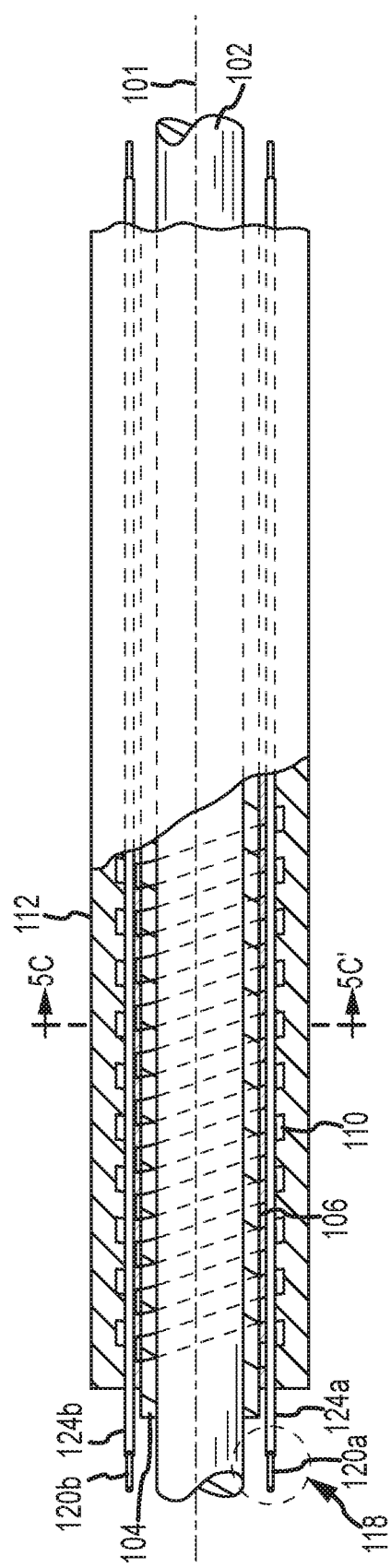
FIG. 4 illustrates the dual braided catheter shaft of FIG. 1A modified to include a steering wire between inner and outer braids of the dual braided catheter shaft.
Figure 5A:
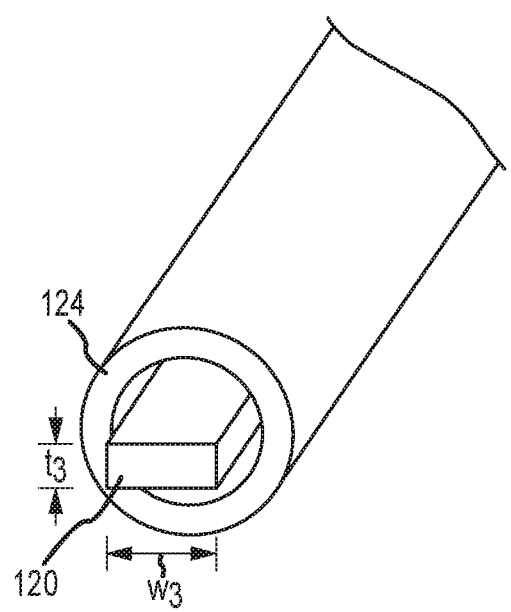
FIG. 5A illustrate a steering wire and tubular sheath that may be disposed between inner and outer braids of a dual braided catheter shaft.

FIG. 4 illustrates the catheter shaft 100 of FIG. 1A as modified to include first and second steering wires 120*a*, 120*b* (hereafter 120, unless specifically referenced), which are disposed between the inner braid 106 and outer braid 110 of the catheter shaft 100. In the present embodiment, first and second steering wires are each encased within a sleeve 124 prior to being disposed between the braids. FIG. 5A illustrates one embodiment of the steering wire 120 as disposed within the sleeve 124. As shown, the steering wire 120 may be a flat wire formed from metal such as stainless steel. As with the inner and outer braid 106, 110, the flat wire may have a thickness $T_3$ that is less than its width $W_3$. Using the flat wire with a thickness less than its width will reduce the overall profile of the device. Thus, as may be appreciated, utilization of a flat wire may allow for providing a steering wire having necessary tensile properties while minimizing the overall thickness of the shaft. However, other cross-sectional shapes may be utilized. The thickness of the flat wire 120 is typically aligned with the longitudinal axis 101 of the core rod 102 and/or internal lumen of the inner jacket 104 once the core rod is removed. In one arrangement, the flat wire has a thickness $t_3$, which may be between about 0.002 and 0.008 inches and a width $w_3$ that may be between about 0.004 and 0.020 inches. As shown, the wire 120 is disposed within an internal lumen of the sleeve 124. In the present arrangement, the sleeve 124 is formed of a polymer material that may correspond to the polymer material of the inner and/or outer jackets. In this regard, when the inner or outer jacket is extruded onto the shaft, the outer surface of the sleeve 124 may re-melt or reflow thus securely adhering the sleeve in its desired position.

Referring again to FIG. 4, it is noted that the steering wire 120 and encasing sleeve 124 (hereafter pull wire assembly 118) each extend axially along the length of the shaft 110 substantially parallel to the longitudinal axis 101 of the core rod 102/internal lumen of the inner jacket. As shown, the pull wire assemblies 118 are disposed on the outside of the inner braid 106. It will be appreciated that these pull wire assemblies 118 may be disposed directly on the outside of the inner braid prior to extruding the intermediate layer onto the catheter shaft. Alternatively, the pull wire assemblies 118 may be placed on an outside surface of the intermediate jacket 108 after intermediate jacket is extruded over the inner braid 106. In either arrangement, the pull wire assemblies 118 may be tensioned or adhered in place to maintain their positional relationship with the shaft while an outer braid layer is applied.

Figure 5B:
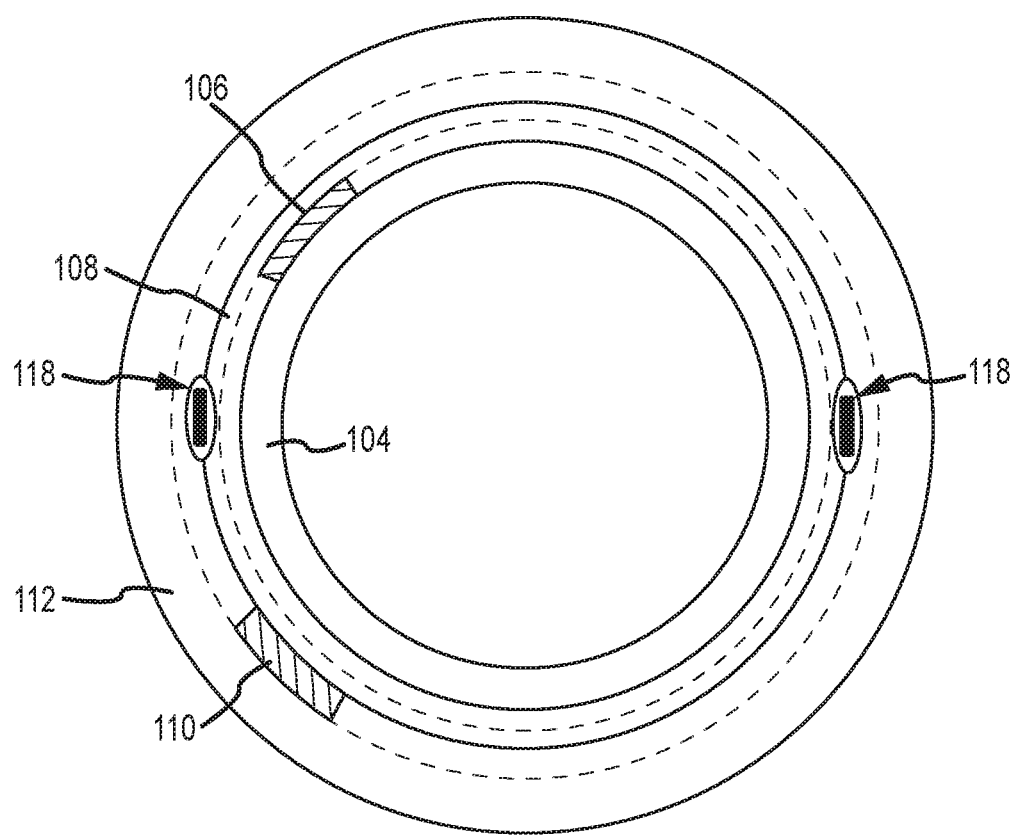
FIG. 5B illustrates a cross-sectional view of the dual braided catheter shaft of FIG. 4.

The outer braid 110 is wound around the outside surface of the intermediate layer and the pull wire assemblies 118 (i.e., disposed inside or outside of the intermediate layer) and thereby encapsulate the pull wire assemblies 118 between the inner and outer braids 106, 110 along at least a portion of the length of the shaft. Such encapsulation is illustrated in the cross-sectional view of FIG. 5B. In such an arrangement, the pull wire assemblies 118 are disposed between the helically wound inner braid 106 and outer braid 110. As illustrated, the steering wire assembly is preferably at least partially embedded within the intermediate jacket 108. The helically wound inner braid, as shown in phantom except for its exposed end, is likewise embedded in the intermediate jacket 108. The outer braid 110 wraps around the outside surface of the intermediate jacket 108 and around wire assemblies 118. Likewise, the outer braid 110, as shown in phantom except its exposed end, is embedded within the outer jacket 112.

Once formed, the steering wires 120A, 120B are operative to move axially along the length of the shaft. That is, the wires 120A, 120B are operative to move relative to the inner and outer braids. In this regard, the sleeve 124 maintains a lumen that permits the movement of these wires relative to the remainder of the shaft. The entirety of the sidewall of sleeve 124 typically does melt though during the reflow procedure and thereby remains after the reflow process. Even in instances where the sleeve melts during the reflow process, the wires may be removed from the sleeve (e.g., the wires may be coated with a release agent) and may be replaced with wires having smaller dimensions. In the latter arrangement, the wires initially disposed within the sleeve 124 are set-up wires that are removed after reflow and replaced with smaller dimension pull wires 120A, 120B.

While the embodiments of FIGS. 1A, 2A-2D, and 4-5C illustrate the encapsulation of the steering wires between inner and outer braids of a catheter shaft where the braids are wound on a core rod or mandrel and the layers of polymer extruded onto that mandrel, it will be appreciated that in other arrangements, other techniques may be utilized to generate a shaft having one or more steering wires encapsulated between an inner and outer braid.

FIGS. 6A-6G illustrate the formation of a catheter shaft formed using a re-melt process. Initially, an inner jacket 604 is disposed on the outside surface of a core rod 602. Stated otherwise, the core rod 602 is disposed through an inner lumen (not shown) of the cylindrical inner jacket/cylinder 604. Again, this inner jacket 604 may be formed of any polymer material as set forth above. In one arrangement, the inner jacket 604 is formed of an etched PTFE material to assist in a re-melting process as discussed herein.

Once the inner jacket 604 is disposed over the core rod 602, an inner braid 606 may be wound around or stretched over an outside surface of the inner jacket 604. See FIG. 6B. In the latter regard, a preformed helical wire may be placed over an outside surface of the inner jacket 604. Once the wire is placed over the outside surface, the wire may be stretched to tighten the coils of the wire 606 about the outside surface of the inner jacket 604. In this regard, a first end of the wire 606 may be fixedly attached near a first end of the shaft (not shown), and the second end may be stretched to tighten the coils. In conjunction with such tightening, it will be appreciated that the pic rate and/or spacing and/or angular disposition of the coils may be adjusted along the length of the wire 606 between first and second ends of the shaft. Again, to reduce the thickness of the wall of the catheter shaft, the first wire 606 may be a flat wire, as discussed above.

Figure 6B:
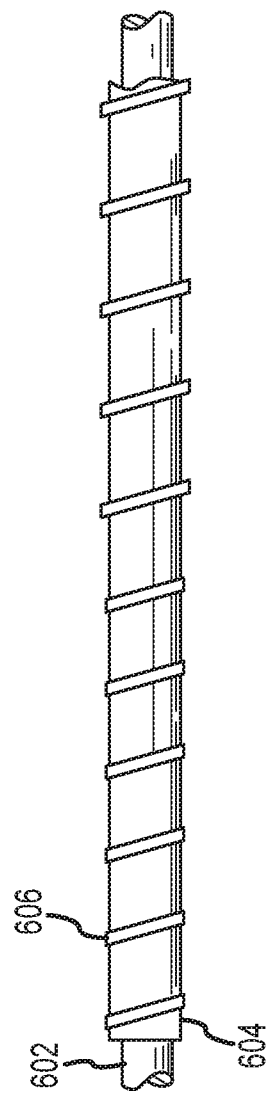
Figure 6C:
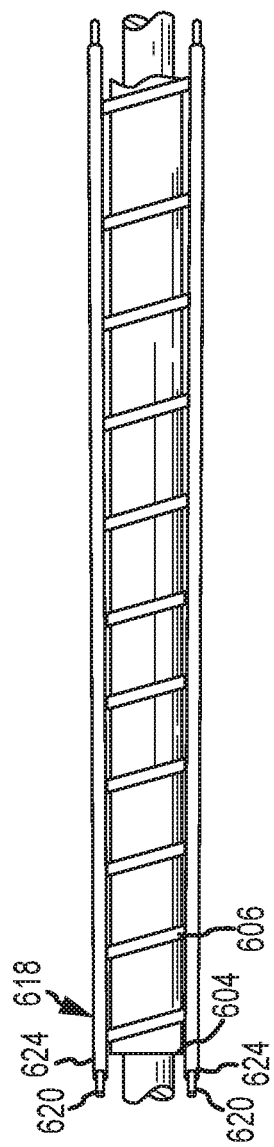

Once the second end of the inner braid 606 is secured, at least a first pull wire assembly 618 may be disposed on an outside surface of the inner braid 606, as illustrated in FIG. 6C and FIG. 7. Typically, at least first and second pull wire assemblies 618 are disposed on diametrically opposing outside surfaces of the inner braid 606. However, it will be appreciated in other arrangements, a single pull wire assembly or additional (e.g., four) pull wire assemblies may be disposed around the circumference of the shaft 600. Again, the pull wire assemblies 618 include a steering wire 620 disposed within a polymer sleeve 624. In the present embodiment, the polymer sleeve 624 is made of an etched PTFE material. These pull wire assemblies 618 are affixed to this outside surface in any manner that permits the wires to maintain a desired positional relationship during the application of subsequent layers. In one arrangement, the steering wire assemblies 618 are adhered along their length on the outside surface of the inner braid 606.

Figure 6D:
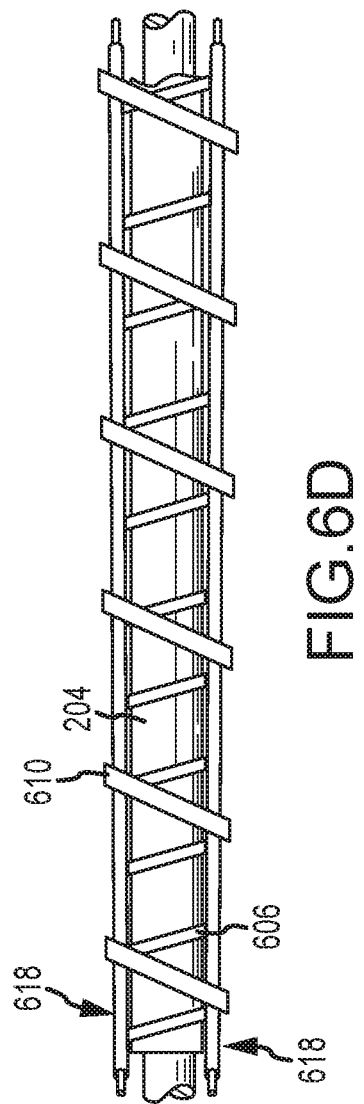

Once the pull wire assemblies 618 are affixed to the outside surface of the inner braid 606, the outer braid 610 may be applied around the outside surface of the pull wire assemblies 618 and the inner braid 606, as illustrated in FIG. 6D. Again, a coiled, helical wire (e.g., a flat wire) may be wound around or disposed about this outside surface and/or stretched to tighten the coils of this wire about the pull wire assemblies 618 and inner braid 606. In the illustrated embodiment, the inner braid 606 and outer braid 610 are shown as being wound in an opposite rotational sense. However, it will be appreciated that these braids 606, 610 may be wound in a corresponding rotational sense. Furthermore, it will be appreciated that differing pic rates may be utilized along different axial sections of the inner and/or outer braids. For example, FIG. 2B illustrates a first pic rate of the inner braid 204 in a first section $s_1$ of the catheter and a second pic rate of the inner braid 204 in a second section $s_2$ of the catheter. Likewise, FIG. 2D illustrates a first pic rate of the outer braid 208 in a first section $s_3$ of the catheter and a second pic rate of the outer braid 208 in a second section $s_4$ of the catheter. Similar variation of the pic rates of the inner and outer braids 606 and 610 of the catheter of FIGS. 6A-6G may be utilized to provide greater flexibility at a distal end of the catheter and/or a greater axial rigidity at the proximate end.

Once the outer braid 610 is secured in a desired location, an outer jacket 112 is disposed over the outside surface of the outer braid 610. See FIG. 6E. At this time, the various different layers, braids and pull wire assemblies of the catheter shaft 600 are in their desired positions. However, to maintain these positions, it may be desirable or necessary to re-flow/re-melt the inner jacket, outer jacket, and outside surfaces of the sleeves 624 of the pull wire assemblies 618. Further, a heat-shrink tube may be disposed around an outside surface of the outer jacket 612 to apply a compressive force between the heat-shrink tube and the core rod 602. This entails raising the temperature of the outer jacket, inner jacket, and steering assembly sleeves to the point that these members reflow and thereby at least partially melt together. At such time, the outer jacket and inner jacket may flow into contact between the braids of the inner and outer braids 606, 610. Once cooled, the inner and outer jackets may become a unitary or integral member.

Figure 6F:
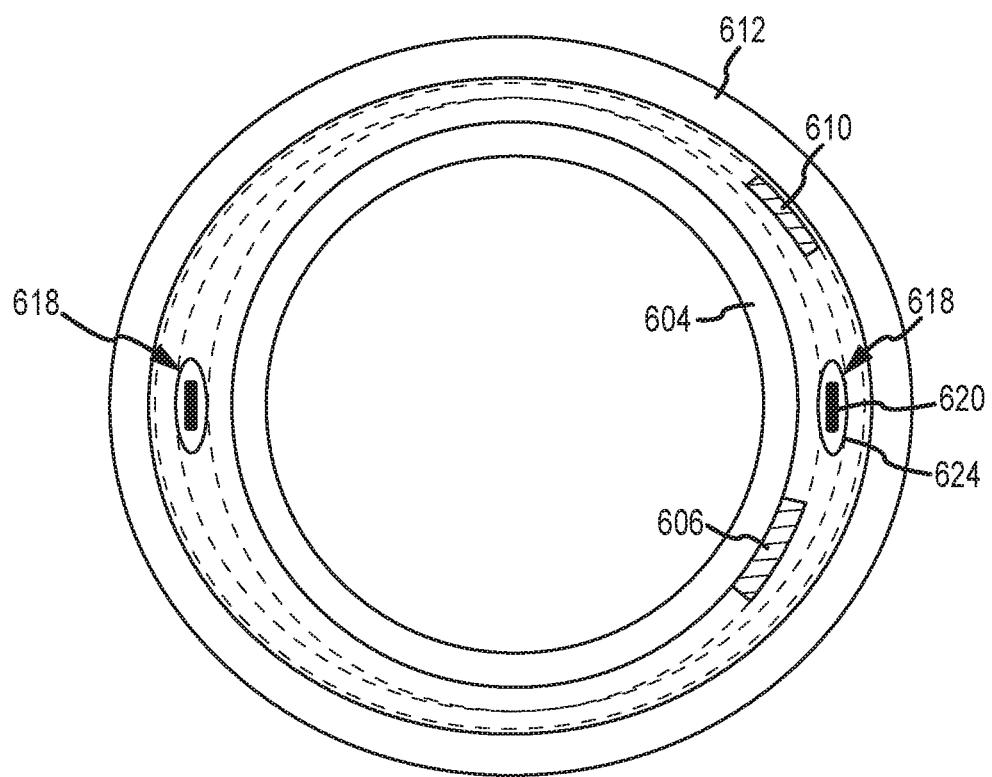
Figure 6G:
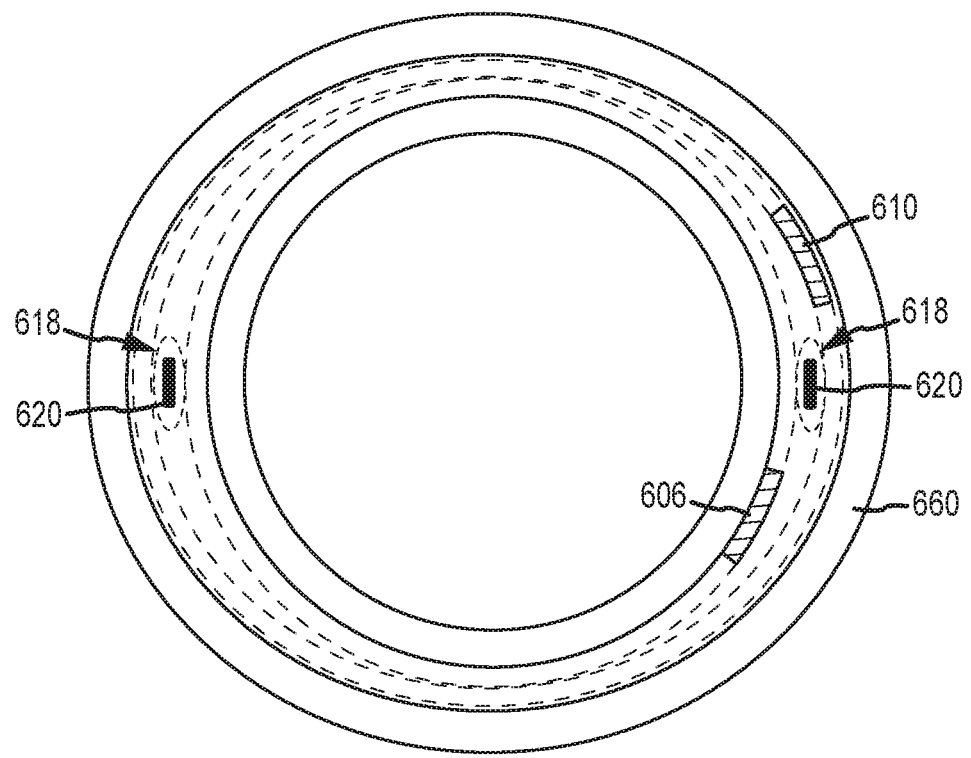

FIG. 6F shows a cross-sectional end view of the shaft of FIGS. 6A-6E prior to the re-flow process. As shown, the helically wound inner braid is disposed directly over the outside surface of the inner jacket 604. The outer braid 610 encapsulates the steering wire assemblies between the outside surface of the inner braid 606 and the inside surface of the outer braid 610. Further, the outer jacket 612 is disposed around the outside surface of the outer braid 610. FIG. 6G illustrates the same cross-sectional area after the re-melt process. As shown, the interfaces between the outside surface of the inner jacket, the inside surface of the outer jacket, and the outer surfaces of the pull wire assembly sheathes are at least partially removed, once the separate material layers at least partially melt together. At this time, these re-melted jackets effectively define a unitary or integral sidewall 660 embedding the braids 606, 610 and steering wires 620.

While disposing the pull wire assemblies between the inner and outer braids of the catheter shaft provides a secure attachment for the steering wires, it will be appreciated that in order to interconnect the distal ends of each steering wire to a steering assembly (e.g., pull ring, etc.) that these wires must exit from their encapsulation between the inner and outer braids. FIG. 7 illustrates one-exemplary embodiment of an arrangement where the pull wire assemblies 618 exit from beneath the outer braid 616 for interconnection to a pull ring 630 interconnected to a distal portion of a catheter apparatus. As shown, a distal end portion 650 of a dual braided shaft is free of the outer braid 610. Stated otherwise, the outer braid 610 does not extend to a distal tip 640 of the catheter apparatus. Rather, the outer braid 610 terminates a predetermined distance prior to the distal tip of the catheter apparatus. As shown, the inner braid 606 may extend over this end portion 650 and terminate at the tip 640. In various arrangements, the tip 640 may include, for example, an electrode (e.g., mapping, ablation, etc.) and/or an opening 642 to the central lumen of the catheter shaft.

As illustrated, each the pull wire assembly 618 extends from beneath the end of the outer braid 610 and extends along an outside surface of the inner braid 606. The sheath 624 of the pull wire assembly terminates prior to the pull ring 630 such that a distal end portion of the steering wire 620 is exposed for connection to the pull ring 630. In various arrangements, the pull wire assemblies 618 may be secured to the outside surface of the distal end portion 650 utilizing, for example, heat shrink tubing or other outer material layers. Further, in other arrangements, the catheter shaft may be formed such that the pull wire assemblies 618 exit through an interior surface/lumen of the catheter. That is, while majorities of the length of the pull wire assemblies 618 are encapsulated between the inner and outer braids, the distal ends of these assemblies may pass through the inner braid into the central lumen of the shaft near its distal end for interconnection to a steering assembly such as a pull ring.

In order to secure the distal end of the outer braid 610, the last few windings of this outer braid 610 may be wound adjacent to one another and adhered together. Additionally or alternatively, a stop tube 632 (e.g., heat shrink wrapping shown in phantom) may be disposed around the last few windings of the outer braid 610 and over the outside surface of the outer jacket 612. However, it will be appreciated that various different mechanisms for securing the end of the braid may be utilized.

Figure 8:
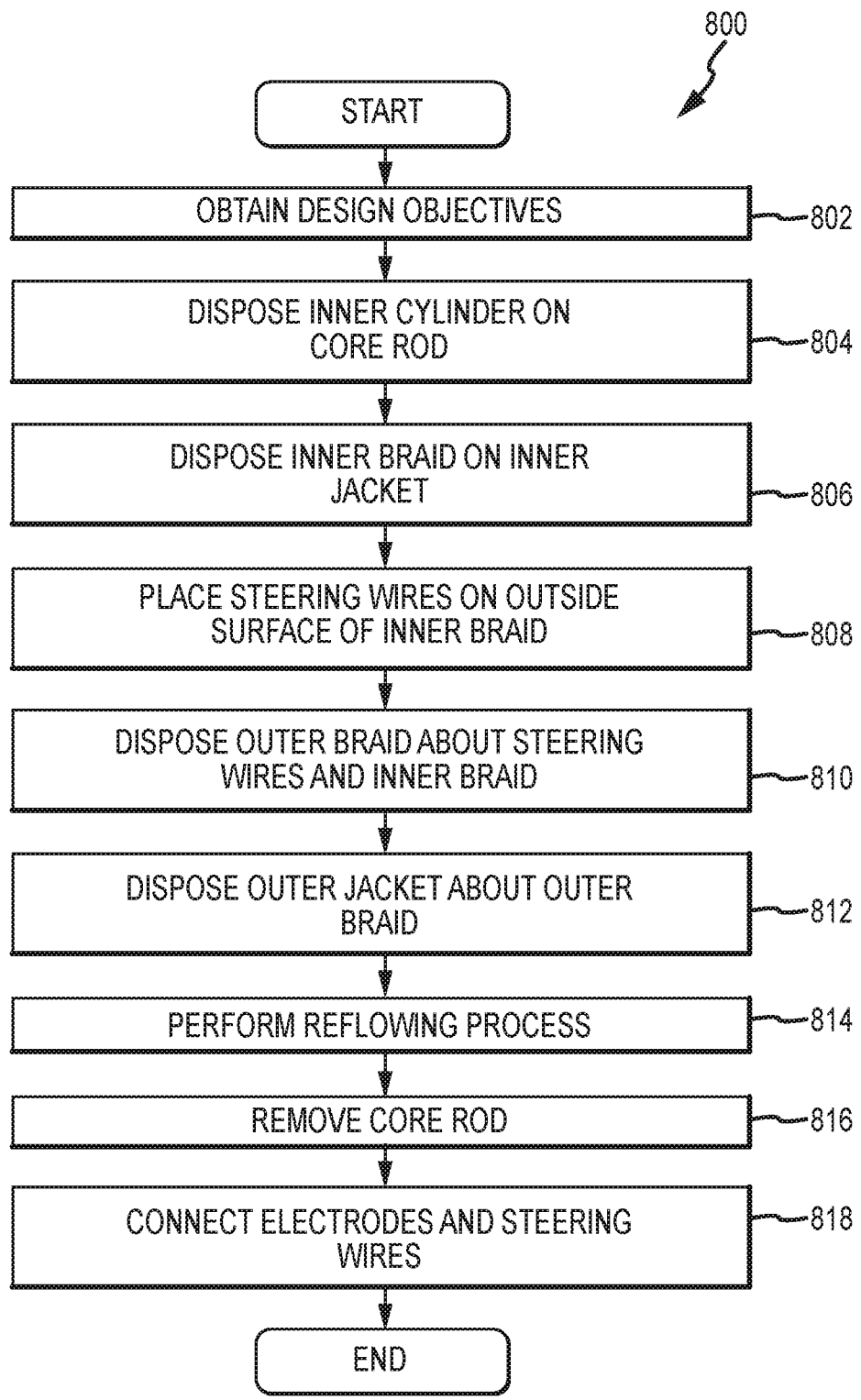
FIG. 8 is a flow chart illustrating a process for constructing a dual braided shaft in accordance with the present invention.

FIG. 8 illustrates a process for designing and constructing a catheter shaft where one or more steering wires are disposed between inner and outer braids of the shaft. The illustrated process (800) is initiated by obtaining (802) design objectives for the catheter shaft. In this regard, different shaft platforms may be used for different catheter applications. For example, a particular catheter application may dictate the need for greater flexibility near the distal portion of the catheter and a stiffer proximal portion thereof. Likewise, the catheter application may dictate a particular limit on the inside and/or outside diameters of the catheter. The designer can then determine the inner and outer braid system design parameters. For instance, the inner braid system may be used primarily to address considerations of axial rigidity. In contrast, the outer braid may be used primarily to address considerations of torsional rigidity. In this regard, durometer hardness of the inner and outer jackets may be selected to provide desired design objectives. Furthermore, it will be appreciated that in various catheter designs the outer jacket may utilize different materials along the length of the shaft. For instance, a distal end of the shaft may utilize a low durometer hardness (e.g., 25D, 35D) polymer material such a PEBEX®, a middle section may utilize a higher durometer hardness material (e.g., 40D-60D) and a the proximal section of the catheter may utilize a yet harder material and/or different material such as, for example, a nylon material. In any arrangement, once the design parameters are identified, construction of the shaft begins by disposing (804) an inner jacket/cylinder on a core rod. The inner braid is then wound around or otherwise disposed (806) about the outside surface of the inner jacket. Such disposition may include the securing of one end and/or stretching of the braid along its length to tighten the coils and/or define desired pic rates along the length of the coil. One or more pull wire assemblies is then placed (808) on the outside surface of the inner braid along the length of at least a portion of the catheter shaft. An outer braid is then wound around or disposed (810) on the outside surface of the inner braid to encapsulate the pull wires between the inner and outer braids. Again, this outer braid is secured in a desired fashion. An outer jacket is then disposed (812) over the outer braid to finish the initial lay-up of the shaft.

A re-melting process is performed (814) on the shaft to at least partially melt the inner and outer jackets together and/or integrate the sleeves of the pull wire assemblies into the unitary or integral structure. It will be appreciated that such a re-melting process may include heat shrinking the outer jacket relative to the inner core rod to apply compressive force between the outside surface of the outer jacket and the inside surface of the inner jacket. Finally, the core rod is removed (816). The distal ends of the pull wire assemblies are then connected (818) to a steering assembly to form a finished catheter product. In an alternate arrangement, the pull wire assemblies may include set-up wires. That is, rather than having pull wires disposed within a sleeve, a removable set-up wire is disposed in the sleeve. Once the shaft is formed (e.g., re-melted) the set up wires may be removed from the sleeves. The removal of the set-up wires leaves lumens extending between the braids. Pull wires pre-attached to a steering assembly (e.g., pull ring) may then be inserted through these lumens. In any arrangement, it will be appreciated that electrodes and/or various connecting wires may be disposed through the inner lumen in order to form a catheter for a particular application. Additional re-melting/reflowing steps may be required to adhere various elements to the inner lumen of the catheter shaft and/or to connect various elements to the distal end of the catheter shaft. It will be appreciated that a number of conventional finishing processes may be implemented in this regard.

Although a number of embodiments of this invention have been described above with a certain degree of particularity, those skilled in the art could make numerous alterations to the disclosed embodiments without departing from the spirit or scope of this invention. For instance, while the embodiments discussed above utilize two pull wire assemblies disposed between the inner and outer braids, it will be appreciated that other embodiments may utilize a single pull wire or multiple pull wire assemblies (e.g., four pull wire assemblies). Such multiple pull wire embodiments may provide additional directional control or deflection of the distal end of a catheter device. Further, all directional references (e.g., upper, lower, upward, downward, outer, inner, axial, radial, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for use in constructing a catheter shaft, comprising:
    disposing an inner braid structure about an outside surface of a first cylindrical layer of polymer;
    placing a pull wire on an outside surface of the inner braid structure, wherein the pull wire extends substantially parallel to a longitudinal axis of the first cylindrical layer of polymer;
    disposing an outer braid structure about the outside surface of the inner braid structure and the pull wire, wherein at least a portion of a length of the pull wire is encapsulated between the inner braid structure and the outer braid structure;

disposing a second cylindrical layer of polymer about an outside surface of the outer braid structure; and at least partially remelting the first cylindrical layer of polymer and the second cylindrical layer of polymer to at least partially embed the inner braid structure in the first cylindrical layer of polymer and to at least partially embed the outer braid structure in the second cylindrical layer of polymer.

2. The method of claim 1, wherein the remelting further comprises:

reflowing an outside surface portion of the first cylindrical layer of polymer at least partially through the inner braid structure;

reflowing an inside surface portion of the second cylindrical layer of polymer at least partially through the outer braid structure.

3. The method of claim 2, wherein the remelting further comprises forming a melt interface between portions of the first cylindrical layer of polymer and portions of the second cylindrical layer of polymer to form an integral sidewall of the catheter shaft.

4. The method of claim 1, wherein the placing of the pull wire further comprises:

placing a tubular sleeve of polymer on the outside surface of the inner braid structure, wherein the tubular sleeve of polymer extends substantially parallel to a longitudinal axis of the first cylindrical layer of polymer and the pull wire is disposed within the tubular sleeve of polymer.

5. The method of claim 4, wherein the remelting further comprises forming a melt interface between the tubular sleeve of polymer and at least one of the first cylindrical layer of polymer and the second cylindrical layer of polymer.

6. The method of claim 1, wherein the disposing the inner braid structure or outer braid structure further comprises one of:

winding a wire directly around an underlying structure; and placing a helically formed wire over an underlying structure and stretching the helically formed wire around the underlying structure.

7. The method of claim 6, wherein the disposing of the inner braid structure comprises varying a pic rate of a first series of windings of the inner braid structure along a length of the first cylindrical layer of polymer.

8. The method of claim 7, wherein the disposing of the outer braid structure comprises varying a pic rate of a second series of windings of the outer braid structure along the length of the first cylindrical layer of polymer.

9. The method of claim 8, wherein the varying of the first pic rate is independent of the varying of the second pic rate, wherein the first series of windings and the second series of windings have different pic rates along the length of the first cylindrical layer of polymer.

10. The method of claim 1, further comprising:

disposing an intermediate cylindrical layer of polymer about the outside surface of the inner braid structure, wherein remelting forms melt interfaces between the first cylindrical layer of polymer, the intermediate cylindrical layer of polymer and the second cylindrical layer of polymer to form an integral sidewall of the catheter shaft.

11. The method of claim 1, further comprising:

extruding the first cylindrical layer of polymer on a mandrel; and extruding the second cylindrical layer of polymer about the outside surface of the outer braid structure.

12. A method for use in constructing a catheter shaft, comprising:

disposing an inner cylindrical braid structure around an outside surface of an inner cylindrical layer of polymer that has a length extending between a proximal portion and a distal portion;

disposing an outer cylindrical braid structure around an outside surface of the inner cylindrical braid structure;

disposing a tubular sleeve of polymer substantially parallel to a longitudinal axis of the inner cylindrical layer of polymer, wherein the tubular sleeve of polymer has an interior pull wire lumen and the tubular sleeve of polymer extends;

disposing an outer cylindrical layer of polymer about the outside surface of the outer cylindrical braid structure, wherein the tubular sleeve of polymer is disposed within the outer cylindrical layer of polymer; and at least partially remelting the inner cylindrical layer of polymer, the outer cylindrical layer of polymer and the tubular sleeve of polymer, wherein the cylindrical layers of polymer and the tubular sleeve of polymer at least partially melt together to define an integral shaft with an embedded pull wire lumen and embedded cylindrical braid structures.

13. The method of claim 12, further comprising:

varying a first braiding parameter of the inner cylindrical braid structure along the length of the inner cylindrical layer of polymer to vary a first mechanical property of the catheter shaft.

14. The method of claim 12, further comprising:

varying a second braiding parameter of the outer cylindrical braid structure along the length of the inner cylindrical layer to vary a second mechanical property of the catheter shaft.

15. The method of claim 14, wherein the varying of the first and second braiding parameters comprises:

independently varying the braiding parameters along the length of the inner cylindrical layer of polymer.

16. The method of claim 15, wherein varying the braiding parameters comprises:

altering a pic rate of the braiding parameters along the length of the inner cylindrical layer of polymer.

17. The method of claim 12, wherein the disposing of the inner cylindrical braid structure or the outer cylindrical braid comprises:

winding a wire around an underlying structure.

18. The method of claim 12, wherein disposing a tubular sleeve of polymer comprises:

disposing the tubular sleeve of polymer on an outside surface of the inner cylindrical braid structure, wherein the outer cylindrical braid structure disposed around the tubular sleeve of polymer.

19. The method of claim 12, further comprising:

disposing an intermediate cylindrical layer of polymer between the inner cylindrical layer of polymer and the outer cylindrical layer of polymer.

20. The method of claim 12, further comprising extruding the inner cylindrical layer of polymer and the outer cylindrical layer of polymer onto underlying structures.

* * * * *